(12) United States Patent
Riether

(10) Patent No.: US 10,012,666 B2
(45) Date of Patent: Jul. 3, 2018

(54) SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Christian Riether, Muehltal (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/665,397

(22) Filed: Mar. 23, 2015

(65) Prior Publication Data

US 2015/0276782 A1    Oct. 1, 2015

(30) Foreign Application Priority Data

Mar. 31, 2014   (EP) .................................... 14162916

(51) Int. Cl.
| | |
|---|---|
| *G01N 35/10* | (2006.01) |
| *G01N 35/00* | (2006.01) |
| *G01N 35/02* | (2006.01) |
| *G01N 35/04* | (2006.01) |

(52) U.S. Cl.
CPC ..... *G01N 35/1081* (2013.01); *G01N 35/0092* (2013.01); *G01N 35/02* (2013.01); *G01N 2035/00445* (2013.01); *G01N 2035/0406* (2013.01); *G01N 2035/0462* (2013.01); *G01N 2035/0477* (2013.01)

(58) Field of Classification Search
CPC .................. G01N 35/1081; G01N 2035/00445
See application file for complete search history.

(56) References Cited

U.S. PATENT DOCUMENTS

| | | |
|---|---|---|
| 3,273,727 A | 9/1966 | Rogers et al. |
| 2,653,485 A | 4/1972 | Donlon |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grechsch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Sean E Conley
*Assistant Examiner* — Matthew D Krcha
(74) *Attorney, Agent, or Firm* — Roche Diagnostics Operations, Inc.

(57) ABSTRACT

A sample distribution system having a transport surface on which sample container carriers can be moved is presented. The sample distribution system has ambient-condition influencing device in order to influence ambient conditions over a sub-region of the transport surface in such a way that samples can be kept there for a certain time without impairment.

11 Claims, 2 Drawing Sheets

(56) References Cited

U.S. PATENT DOCUMENTS

| | | |
|---|---|---|
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Bah |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,211,543 B2 | 12/2015 | Ohga et al. |
| 9,239,335 B2 | 1/2016 | Heise et al. |
| 2002/0009391 A1 | 1/2002 | Marquiss et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1* | 3/2008 | Rund .................. G01K 3/00 374/102 |
| 2008/0131961 A1* | 6/2008 | Crees .................. B01L 9/52 435/309.1 |
| 2008/0286162 A1 | 11/2008 | Onizawa et al. |
| 2009/0004732 A1 | 1/2009 | LaBarre et al. |
| 2009/0022625 A1* | 1/2009 | Lee .................. B01L 7/52 422/68.1 |
| 2009/0081771 A1 | 3/2009 | Breidford et al. |
| 2009/0128139 A1 | 5/2009 | Drenth et al. |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276781 A1 | 10/2015 | Riether et al. |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 6/1994 |
| EP | 0775650 A1 | 5/1997 |
| EP | 0896936 A1 | 2/1999 |
| EP | 0916406 A2 | 5/1999 |

(56) References Cited

FOREIGN PATENT DOCUMENTS

| | | |
|---|---|---|
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1966 |
| JP | 03-192013 A | 8/1981 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 01-266860 A | 10/1989 |
| JP | H02-87903 A | 3/1990 |
| JP | 3-112393 A | 5/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-190400 A | 9/2013 |
| JP | 2013-1720009 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013177163 A1 | 11/2013 |
| WO | 2014/059134 A1 | 4/2014 |
| WO | 2014/071214 A1 | 5/2014 |

\* cited by examiner

SAMPLE DISTRIBUTION SYSTEM AND LABORATORY AUTOMATION SYSTEM

CROSS-REFERENCE TO RELATED APPLICATIONS

This application claims priority to EP 14162916.2 filed Mar. 31, 2014, which is hereby incorporated by reference.

BACKGROUND

The present disclosure generally relates to a sample distribution system and to a laboratory automation system.

The present invention addresses the problem of providing a sample distribution system and a laboratory automation system which allow the flexible transport and flexible processing of samples, particularly in terms of dynamically variable waiting times until a possible treatment and/or processing of the samples in the stations.

SUMMARY

According to the present disclosure, a sample distribution system for distributing sample containers between pre-analytical, analytical and/or post-analytical stations of a laboratory automation system is presented. The sample distribution system can comprise a plurality of sample container carriers. The sample container carriers can comprise at least one magnetic element and can receive a sample container. The sample distribution system can further comprise a transport device. The transport device can comprise a transport surface to carry the sample container carriers and a plurality of electromagnetic actuators arranged in a stationary manner under the transport surface. The electromagnetic actuators can move a sample container carrier arranged on the transport surface over the transport surface by applying a magnetic force to the sample container carrier. The transport device can also comprise a control device to activate the electromagnetic actuators such that a sample container carrier is moved over the transport surface along a predeterminable path of movement. Finally, the sample distribution system can comprise ambient-condition influencing device to influence at least one ambient condition of a sub-region of the transport surface.

Accordingly, it is a feature of the embodiments of the present disclosure to provide a sample distribution system and a laboratory automation system which allow the flexible transport and flexible processing of samples with dynamically variable waiting times until a possible treatment and/or processing of the samples in the stations. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
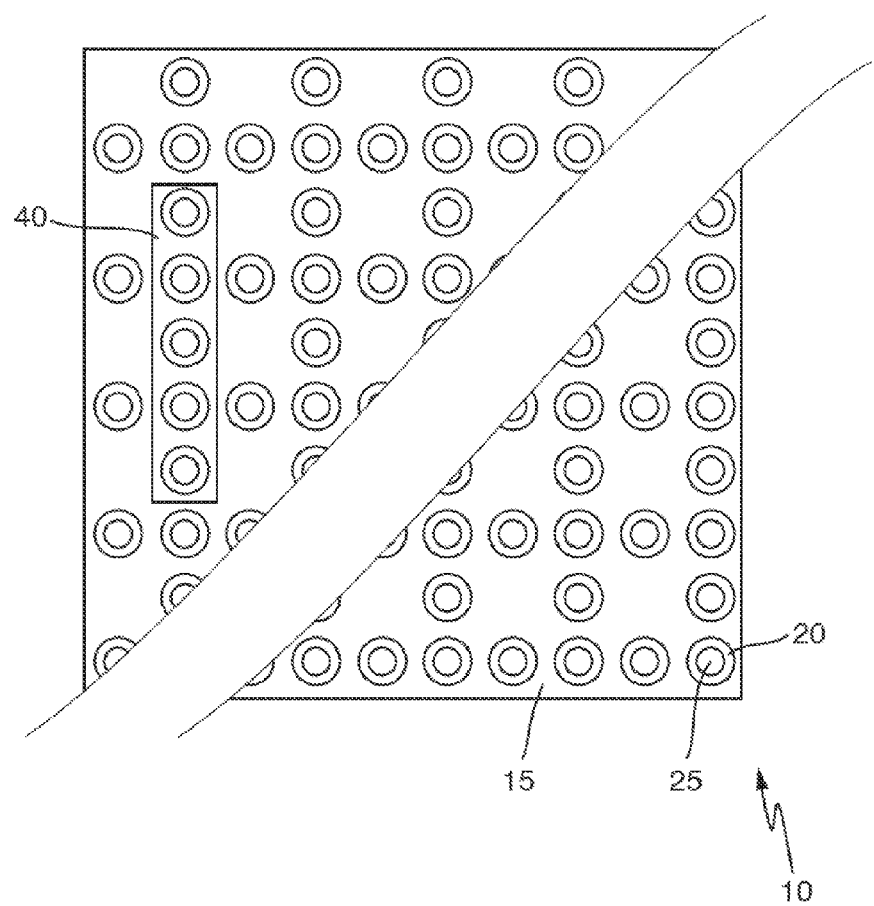
FIG. 1 illustrates a sample distribution system in a schematic plan view according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The present disclosure relates to a sample distribution system to transport sample containers between pre-analytical and/or analytical and/or post-analytical stations of a laboratory automation system. A pre-analytical station can usually serve for the pre-processing of samples or sample containers. An analytical station may be designed for example for using a sample or part of the sample and a reagent to generate a measurable signal, on the basis of which it can be determined whether the analyte is present, and if so in what concentration.

A post-analytical station can usually serves for the post-processing of samples or sample containers. The pre-analytical, analytical and post-analytical stations may for example have at least one station chosen from the group of following stations: a cap-removing station for removing caps or closures on sample tubes, a cap-applying station for applying caps or closures to sample tubes, an aliquoting station for aliquoting samples, a centrifuging station for centrifuging samples, an archiving station for archiving samples, a pipetting station for pipetting, a sorting station for sorting samples or sample tubes, a sample-tube-type determining station for determining a type of sample tube and a sample-quality determining station for determining the quality of a sample.

The sample distribution system can comprise a number of sample container carriers, for example, identical sample container carriers, for example, several tens to several hundreds of sample container carriers. The sample container carriers can be respectively designed for receiving and fixing a sample container, usually in the form of a sample tube.

The sample container carriers can respectively comprise at least one magnetically active element, for example in the form of one or more permanent magnets and/or ferromagnetic material.

The sample distribution system can further comprise a transport device. The transport device can comprise an even, horizontally aligned transport surface, which can be designed for carrying the sample container carriers. The transport device can further comprise a plurality of electromagnetic actuators, which can be for example distributed in rows and columns and can be arranged in a stationary manner under the transport surface. The electromagnetic actuators can be designed for moving a respective sample container carrier that can be located on the transport surface two-dimensionally on the transport surface by exerting a magnetic force on the respective sample container carrier or its magnetically active element. The electromagnetic actuators may be electromagnets.

The sample distribution system can further comprise a control device, which can be designed for activating the electromagnetic actuators in such a way that a sample container carrier can move on the transport surface along a freely predeterminable path of movement. The control device may be for example a computer, a processor, a programmable logic controller (PLC) or some other system performing control tasks. For example, the control device may also have a memory, stored in which can be program code that can determine the behavior of the control device.

The sample distribution system can further comprise an ambient-condition influencing device, which can be designed for influencing or changing, for example controlling or regulating, at least one ambient condition of at least one sub-region of the transport surface or over the at least one sub-region or of a defined volume over the at least one sub-region.

The sample distribution system can make it possible to keep samples under monitored ambient conditions during a specific time on or over the sub-region of the transport surface. For example, the ambient-condition influencing device may be designed for influencing, for example cooling, a temperature of an atmosphere of the sub-region. Consequently, a temperature that prevents, or at least slows down, undesired chemical reactions in the samples may be brought about over the sub-region of the transport surface.

The ambient-condition influencing device may be designed for locally influencing the at least one ambient condition of the sub-region of the transport surface. This may mean that the ambient conditions can only be influenced in a sharply delimited manner within or above the sub-region, whereas normal ambient conditions, or ambient conditions uninfluenced by the ambient-condition influencing device, prevail outside the sub-region. This can for example reduce energy consumption necessary for operating the ambient-condition influencing device. The ambient-condition influencing device may have a number of thermocouples for influencing the temperature, which can be assigned to the sub-region of the transport surface. For example, such thermocouples may be arranged under the transport surface, on the transport surface, over the transport surface or to the side(s) of the sub-region. Such thermocouples may be, for example, Peltier elements. These can make it possible for the temperature to be influenced in an energy-saving manner without producing noise. For example, they can make cooling possible.

The ambient-condition influencing device may be designed for influencing a composition of an atmosphere of the sub-region. This may serve the purpose of achieving a particular gas composition of the atmosphere, by which harmful processes in the samples, for example chemical reactions, can be prevented, or at least slowed down. For this purpose, a chemically inert gas such as nitrogen or a noble gas may for example be added or used.

The ambient-condition influencing device may have a housing, which can be arranged over the sub-region of the transport surface and can cover over the sub-region. In this way, an atmosphere to be influenced can be spatially delimited from an atmosphere located outside the sub-region. This can make possible resource- and energy-saving conditioning of the atmosphere with regard to the parameters to be influenced, such as, for example, the temperature or composition, without continuous mixing with a surrounding atmosphere taking place.

The housing may be designed in such a way that it can enclose an air space or an (air) volume over the sub-region on a number of sides (not necessarily on all sides). This can make possible particularly effective shielding of the atmosphere located within the housing. An inner height of the housing over the transport surface may be larger than the height of a sample container carrier with a sample container received therein. This can make it possible for the sample container carriers with corresponding sample containers to be safely moved in, without the risk of them tipping over or being damaged.

According to an embodiment, together with the sub-region of the transport surface arranged thereunder, the housing can form a tunnel over one or more rows and/or columns of electromagnetic actuators. This can make possible simple, for example one-dimensional, control within the sub-region, sample container carriers being able to enter the tunnel at one point and leave the tunnel at another point. A required computing effort for the control can consequently be reduced. The tunnel may also cover over a number of rows and/or columns of electromagnetic actuators.

The housing may have a number of transporting openings, wherein the sub-region transitions to the adjoining part of the transport surface at a respective transporting opening at the same vertical level, i.e. without a level transition. This can make it possible for sample container carriers to enter and leave the housing easily. In this way, it can be possible to omit dedicated transferors, such as, for example, grippers that can introduce or transfer a sample container carrier into the housing.

The ambient-condition influencing device may have a cooling device, which can be designed for cooling air within the housing, for example to temperatures in a range between about 0° C. and about 10° C. For this purpose, a cooling device may be provided within the housing and/or cooled air may be directed into the interior of the housing, to be precise, in particular, through an opening provided for this.

The ambient-condition influencing device may have an air-conditioning device, which can be designed for changing, in particular increasing, a concentration of at least one chemically inert gas, for example, nitrogen, within the housing. In one embodiment, the air-conditioning device may be designed for introducing the chemically inert gas into the interior of the housing.

According to an embodiment, a plurality of air inlets for laterally feeding in air can be assigned to a respective transporting opening of the housing. Alternatively or in addition to this, the housing may have inside a plurality of air inlets for feeding in air, in particular for laterally feeding in air. Laterally feeding in can be understood essentially as meaning horizontally feeding in.

The provision of air inlets at respective transporting openings can allow a certain shielding of the surrounding atmosphere from the atmosphere within the housing to be achieved. In this way, energy can be saved for example. The lateral, that is to say for example horizontal, feeding in of air can achieve the effect that the air is not blown from above directly into a sample container, which is, for example, formed as a vertically upright tube. In this way, excessive mixing of the sample with the fed-in air or splashing of the typically liquid sample over a rim of the sample container can be prevented.

The sample distribution system may have a plurality of air outlets for sucking or evacuating air out from inside the housing. These air outlets may for example be connected to a suitable extractor fan. In this way, a defined air stream between the air inlets and the air outlets can be achieved, so that, for example, air fed in does not escape at the transporting opening of the housing, but can be extracted again by way of the air outlets.

According to an embodiment, a plurality of ambient-condition sensors can be assigned to the sub-region of the transport surface. In this way, ambient conditions can be monitored at relevant points. For example, the ambient-condition sensors may be embodied as temperature sensors and/or sensors for determining an air composition.

The sample distribution system may comprise a temperature measuring device, which can measure temperatures of sample containers placed on the transport surface and/or of samples in the sample containers placed on the transport surface. The temperature measuring device may e.g. be embodied as an infrared thermometer or as an infrared camera. The temperature measuring device may e.g. part of an identification module used to identify sample containers and/or sample container carriers. The temperature measuring device may be integrated into a handling device, e.g. in the form of a gripper used to handle sample containers and/or sample container carriers.

The temperatures of sample containers and/or of samples in the sample containers may be measures when the sample containers and/or the samples in the sample containers enter the subarea. The duration the sample containers and/or samples in the sample containers stay in the subarea may be determined based on the measured entering temperature. A higher measured temperature may result in a longer duration and vice versa.

The control device of the sample distribution system may move such sample containers onto the sub-region of the transport surface, which can have measured temperatures exceeding a threshold temperature value, e.g. about 10° C., or about 15° C., or about 20° C.

The control device of the sample distribution system may determine a residence time based on the measured temperature, wherein the control device can place sample containers in the sub-region of the transport surface during the residence time and remove the sample containers from the sub-region of the transport surface after the residence time has lapsed.

Alternatively or additionally, the sample container carriers may comprise a temperature sensor. The temperature sensor can measure a temperature of the received sample container and/or measure a temperature of a sample in the received sample container. The temperature sensor may e.g. measure a surface temperature of the received sample container at a specific position of the sample container, e.g. at the bottom of the sample container. The temperature sensor may be in direct contact with the sample container.

The sample container carriers may respectively comprise data transmitter. The data transmitter can wirelessly transmit the measured temperature e.g. to a control device of the transport device. The data transmitter may e.g. be Bluetooth data transmitter, RFID (radio-frequency identification) data transmitter, near-field data transmitter and the like. For that purpose the transport device may comprise energy storage for providing the energy needed for data transmission. Alternatively, the data transmitter (and the temperature sensor) may be incorporated as a passive RFID-Tag.

The laboratory automation system can comprise a plurality (for example, between about two and twenty) of pre-analytical and/or analytical and/or post-analytical stations, which can be designed for working on or processing sample containers and/or samples contained in the sample containers. The working or processing may, for example, comprise reading a barcode, removing a cap on the tube, centrifuging the sample, aliquoting the sample, analyzing the sample, and the like. The laboratory automation system can also comprise a distribution system for transporting the sample containers between the pre-analytical, analytical and post-analytical stations.

The control device of the sample distribution system may be designed for determining or calculating a waiting time that can be required, or arises on the basis of capacity utilization of the station, before a sample container and/or a sample in the sample container can be worked on by the station. If the waiting time is at least equal to (or larger than) a lower limit value in terms of time, the control device can move the corresponding sample container, for example in its sample container carrier, into the sub-region of the transport surface by suitable activation of the electromagnetic actuators.

The waiting time may be an expected, planned and/or theoretical waiting time. The waiting time can be determined essentially by a waiting time of the corresponding sample container and/or the sample contained therein for working/processing in the pre-analytical, analytical and post-analytical station. The waiting time may for example be calculated or determined by using specific formulae and/or tables. In the simplest case, the waiting time can be determined from the length of a queue in front of a station.

The lower limit value in terms of time may for example be a value in the time dimension that can represent the maximum time that a sample can spend on the transport surface without undesired influencing of the chemical composition of the sample beyond a tolerable extent having to be expected unless a specific ambient condition is provided, that is to say for example unless cooling and/or increased nitrogen concentration is/are provided. If it is likely that a sample will spend too long on the transport surface, it can be moved by the control device into the sub-region of the transport surface in which it can be possible for it to stay a longer time on account of the specific ambient conditions that prevail there. The lower limit value in terms of time may be for example about five minutes.

The control device may be designed for moving the sample container carrier into the sub-region of the transport surface only whenever the waiting time is less than an upper limit value in terms of time. This may be for example a value of approximately, or exactly, 30 minutes. This can be a value that is frequently found in practice to be the time limit beyond which it is no longer possible for the corresponding sample to be stored without risking chemical changes to the sample, even if it is kept in typical ambient conditions of a sub-region.

The laboratory automation system may have a refrigerator, the control device being designed for moving a respective sample container, for example in its sample container carrier, into the refrigerator if the waiting time is at least equal to (or larger than) the upper limit value in terms of time.

Yet again different ambient conditions than at or in the sub-region of the transport surface typically prevail in a refrigerator, for example a still lower temperature may prevail in the refrigerator, whereby chemical reactions can be prevented even better. If quick further processing of the sample is not to be expected, the sample is therefore preferably not kept in the sub-region but in the refrigerator, in order to be able to last the long waiting time without problem.

Referring initially to FIG. 1, FIG. 1 schematically shows parts of a sample distribution system 10. The sample distribution system 10 can have a transport surface 15, which can provide a flat and even surface. On the transport surface 15, sample container carriers with sample containers respectively contained or received therein, which are not represented in FIG. 1, can be placed and moved.

Underneath the transport surface 15, a plurality of electromagnetic actuators in the form of coils 20 with respective cores 25 can be arranged in rows and columns. It can be possible by the electromagnetic actuators to move sample container carriers on the transport surface 15. Arranged on the transport surface 15 can be a multiplicity of position sensors 30 (see FIG. 2), with which the position of sample container carriers on the transport surface 15 can be determined. To form the surface, the transport surface 15 depicted may also have a flat, two-dimensional covering.

Formed on the transport surface 15 is a sub-region 40, which can extend over part of a single column of electromagnetic actuators 20 and the ambient conditions of which can be influenced in comparison with the ambient conditions outside the sub-region 40. How this takes place is explained below with reference to FIG. 2.

Figure 2:
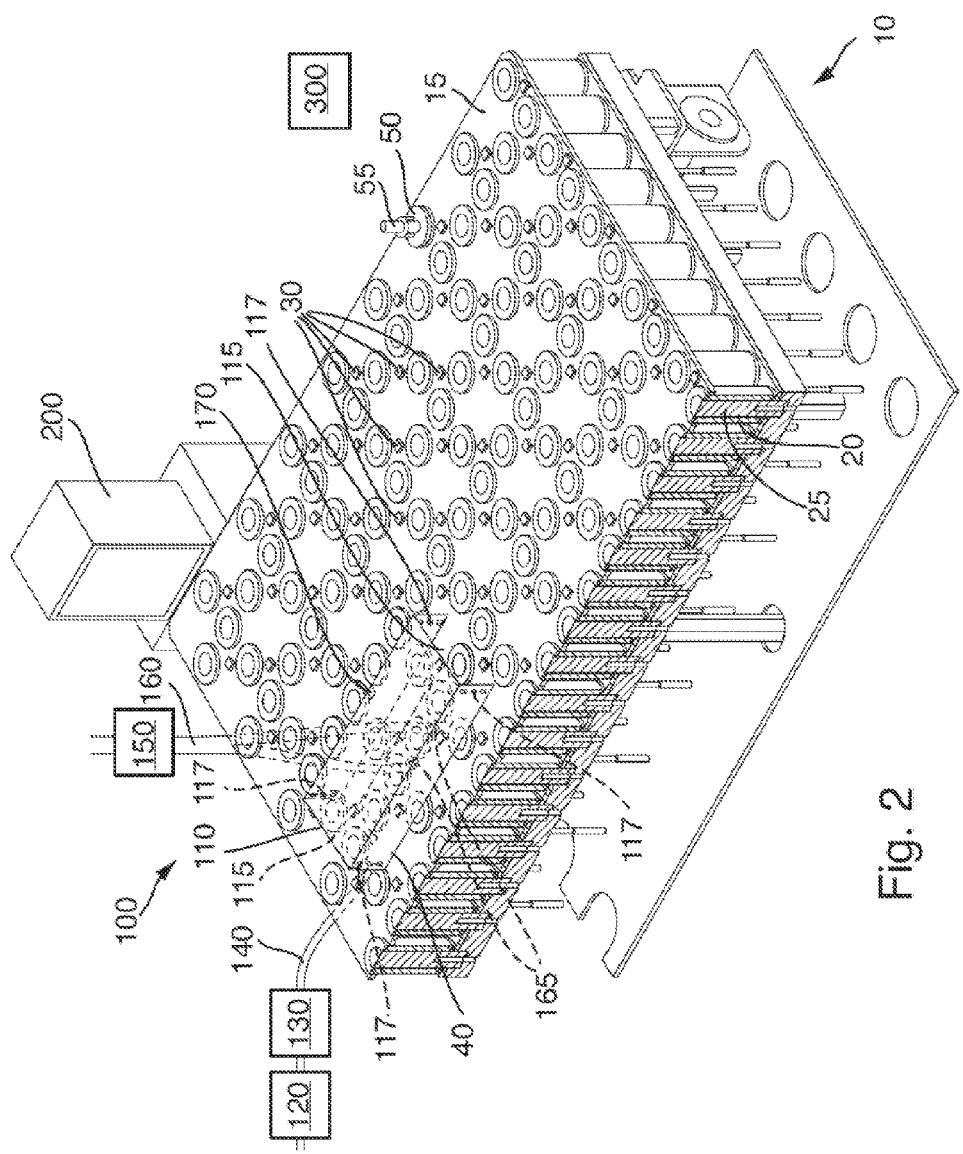
FIG. 2 illustrates the sample distribution system from FIG. 1 in a perspective view according to an embodiment of the present disclosure.

FIG. 2 shows the sample distribution system 10 from FIG. 1 in a perspective view and in further detail. The sample distribution system 10 can be a component part of a laboratory automation system having a plurality of pre-analytical, analytical and post-analytical stations arranged alongside the transport surface 15. The sample distribution system 10 can serve for transporting the sample containers between these stations.

On the transport surface 15 sample container carriers may be placed, wherein only a single sample container carrier 50 is depicted for reasons of simplicity. The sample container carrier 50 can have a magnetic element in the form of a permanent magnet. A sample container in the form of a (sample) tube 55 can be received or contained in the sample container carrier 50. A sample, such as for example a blood plasma sample, may be contained in the tube 55.

The sample distribution system 10 can further comprise ambient-condition influencing device 100, which is described in more detail below. It is possible by the ambient-condition influencing device 100 to influence ambient conditions above the sub-region 40 on the transport surface 15 specifically in such a way that ambient conditions that allow samples to stay for longer without the risk of chemical changes to the samples prevail above the sub-region 40.

The ambient-condition influencing device 100 can have a tunnel-forming housing 110. The housing 110 can completely enclose an air volume above the sub-region 40, apart from two openings 115 at respective longitudinal ends. In this way, a delimitation of the air volume located within the housing 110 with respect to the surroundings can be achieved. Through the openings 115, sample container carriers 50 and sample containers 55 located therein can be moved into the housing 110 and moved out again. In particular, the sample container carriers 50 can also be kept or left in the housing 110. Five coils 20 of the corresponding column form respective discrete positions, wherein the coils 20 can fix the sample container carriers 55, if necessary, and can move the sample container carriers 55, if necessary.

Alongside the respective openings 115, the housing 110 can have a plurality of air inlet openings 117. These can be arranged on respective side walls of the housing 110 and can be designed for blowing air into the interior space of the housing 110 laterally, that is to say in a horizontal direction. As a result, direct blowing into respective sample containers 55 can be avoided. The arrangement alongside the openings 115 can have the effect of producing at the openings 115 a defined atmosphere, which can be set or influenced by the air that can flow out from the air inlets 117.

For supplying the air inlets 117 with correspondingly conditioned air or a correspondingly conditioned gas mixture, the ambient-condition influencing device 100 can have a cooling device 120 and an air-conditioning device 130. The cooling device 120 and the air-conditioning device 130 can be connected to the housing 110 by a line 140, so that correspondingly cooled and conditioned air can flow to the air inlets 117.

The cooling device 120 can be designed for sucking in air from the surroundings and cooling it by approximately 5° C. to 10° C. This cooled air can be supplied to the air-conditioning device 130. The air-conditioning device 130 can be designed for admixing nitrogen with the flowing air, so that the nitrogen concentration can be increased. Consequently, air which has been cooled in comparison with the surrounding atmosphere and the nitrogen fraction of which is increased can enter the line 140. A corresponding atmosphere can consequently also be established in the interior space of the housing 110.

For extracting air from the interior space of the housing 110, the ambient-condition influencing device 100 can have a suction fan 150 and a line 160 connected thereto, which can lead to two air outlets 165 on the bottom area of the housing 110, the bottom area being formed by the sub-region 40 of the transport surface 15. The suction fan 150 can draw air via the line 160 and the two air outlets 165 out of the interior space of the housing 110, so that altogether an air flow from the air inlets 117 to the air outlets 165 can be created. In this way, a defined atmosphere within the housing 110 can be achieved in an advantageous way, with minimal influencing by the surrounding atmosphere.

For monitoring the temperature within the housing 110, an ambient-condition sensor can be provided in the latter in the form of a temperature sensor 170. In this way, the cooling output of the cooling device 120 can be controlled or regulated, so that a desired temperature or temperature difference in relation to the outside temperature is maintained.

Arranged alongside the transport surface 15, the sample distribution system 10 can further comprise a refrigerator 200. A temperature of the refrigerator can be lower than a temperature within the housing 110. It is possible to bring sample container carriers 50 and/or sample containers 55 into the refrigerator 200. Known means that are not presented or discussed any further here, such as for example a gripper, may be used for this purpose.

The sample distribution system 10 can further comprise a control device 300. The control device 300 can comprise a processor and a memory. The memory can store program code that can cause the processor to behave in the way outlined below when it is executed.

The control device 300 can be capable of moving the sample container carriers 50 over the transport surface 15 along paths of movement that can be independent from one another by selective activation of the coils 20.

The control device 300 can calculate for a respective sample container carrier 50 and a sample container 55 located therein (and a sample that is not represented but is comprises in the sample container 55) how long it is likely to be kept on the transport surface 15. For this purpose, the control device 300 may calculate how long it will take until the corresponding sample can be processed by a station. If this staying time or waiting time is below about five minutes, the control device 300 can leave the corresponding sample container carrier 50 at its current position at any point on the transport surface 50, but outside the sub-region 40.

If the expected staying time or waiting time is at least about five minutes, but less than about 30 minutes, the control device 300 can transfer the corresponding sample container carrier 50 into the housing 110, so that the sample can be exposed to a defined atmosphere that can be cooler and can be enriched with nitrogen. In this way, chemical reactions within the sample can be advantageously slowed down. If the expected staying time or waiting time is about 30 minutes or more, the control device 300 can transfer the sample container carrier 50 and/or the sample container 55 into the refrigerator 200.

Concluding, considerably greater flexibility can be achieved by the embodiments of the sample distribution system 10, since waiting times can be dynamically handled without impairments of the samples having to be expected. The provision of the tunnel-forming housing 110 with its defined atmosphere can make it possible to avoid transferring samples into the refrigerator 200. In this way, the refrigerator 200 can for example be dimensioned smaller.

Furthermore, bringing the sample into the refrigerator 200 often needs complex handling tasks, since the refrigerator 200 can be completely isolated from its surroundings. It can consequently be possible to save expenditure on equipment and to save time that would otherwise have to be expended to bring the sample container carrier 50 or sample container 55 into the refrigerator 200 and fetch it out thereof again.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A sample distribution system for distributing sample containers between pre-analytical, analytical and/or post-analytical stations of a laboratory automation system, wherein the sample distribution system comprises:
    a plurality of sample container carriers, wherein the sample container carriers comprise at least one magnetic element and receive a sample container;
    a transport device, wherein the transport device comprises:
        a transport surface to carry the sample container carriers,
        a plurality of electromagnetic actuators arranged in a stationary manner under the transport surface, wherein the electromagnetic actuators move a sample container carrier arranged on the transport surface, over the transport surface by applying a magnetic force to the sample container carrier, and
    a control device configured to activate the electromagnetic actuators such that a sample container carrier is moved over the transport surface along a predeterminable path of movement, wherein the control device of the sample distribution system is configured to determine a waiting time until a respective sample container and/or a sample in the sample container can be processed by a station and wherein the control device is configured to activate the electromagnetic actuators to move a sample container onto a sub-region of the transport surface if the waiting time is at least equal to a lower limit value in terms of time; and
    ambient-condition influencing device to influence at least one ambient condition of the sub-region of the transport surface.

2. The sample distribution system according to claim 1, wherein the ambient-condition influencing device is configured to influences a temperature of the sub-region.

3. The sample distribution system according to claim 1, wherein the ambient-condition influencing device is configured to influence a composition of an atmosphere of the sub-region.

4. The sample distribution system according to claim 1, wherein the ambient-condition influencing device comprises a housing arranged over the sub-region of the transport surface.

5. The sample distribution system according to claim 4, wherein the ambient-condition influencing device has an air-conditioning device to increase a concentration of at least one chemically inert gas inside the housing.

6. The sample distribution system according to claim 1, wherein a plurality of ambient-condition sensors are assigned to the sub-region of the transport surface.

7. A sample distribution system according to claim 1, the sample distribution system comprising:
    a temperature measuring device to measure temperatures of sample containers and/or of samples contained in the sample containers.

8. The sample distribution system according to claim 7, wherein the control device of the sample distribution system is configured to activate the electromagnetic actuators to move a sample container onto the sub-region of the transport surface if the measured temperature exceeds a threshold value.

9. The sample distribution system according to claim 8, wherein the control device of the sample distribution system is configured to determines a residence time based on the measured temperature, wherein the control device is configured to places a sample container in the sub-region of the transport surface during the residence time.

10. The sample distribution system according to claim 1, further comprising,
    a refrigerator, wherein the control device is configured to activate the electromagnetic actuators to move a sample container into the refrigerator if the waiting time is at least equal to an upper limit value in terms of time.

11. A laboratory automation system, the laboratory automation system comprising:
    a plurality of pre-analytical, analytical and/or post-analytical stations to process sample containers and/or samples contained in the sample containers; and
    a sample distribution system for distributing the sample containers between the pre-analytical, analytical and/or post-analytical stations according to claim 1.

* * * * *